United States Patent

Dobrovolny et al.

Patent Number: 6,042,541
Date of Patent: Mar. 28, 2000

[54] CLAMPING DEVICE FOR A SURGICAL RETRACTOR

[75] Inventors: Walter J. Dobrovolny, St. Paul; Todd W. Sharratt, Cottage Grove; Steven M. LeVahn, St. Paul, all of Minn.

[73] Assignee: Minnesota Scientific, Inc., Minneapolis, Minn.

[21] Appl. No.: 09/200,685

[22] Filed: Nov. 25, 1998

Related U.S. Application Data

[60] Continuation-in-part of application No. 09/048,616, Mar. 26, 1998, abandoned, which is a division of application No. 08/541,689, Oct. 10, 1995, Pat. No. 5,741,210.

[51] Int. Cl.⁷ ................................................. A61B 17/02
[52] U.S. Cl. ........................................... 600/228; 600/330
[58] Field of Search ................................... 600/227, 228, 600/230

[56] References Cited

U.S. PATENT DOCUMENTS

| | | |
|---|---|---|
| 1,084,379 | 1/1914 | Wile . |
| 1,464,308 | 8/1923 | Copony . |
| 1,839,726 | 1/1932 | Arnold . |
| 2,670,732 | 3/1954 | Nelson . |
| 2,893,378 | 7/1959 | Cooper . |
| 3,046,072 | 7/1962 | Douglass, Jr. et al. . |
| 3,221,743 | 12/1965 | Thompson et al. . |
| 3,638,973 | 2/1972 | Poletti ........................................ 285/184 |
| 3,749,088 | 7/1973 | Kohlmann . |
| 3,810,462 | 5/1974 | Szpur . |
| 3,965,890 | 6/1976 | Gauthier . |
| 4,143,652 | 3/1979 | Meier et al. . |
| 4,254,763 | 3/1981 | McCready et al. . |
| 4,355,631 | 10/1982 | LeVahn . |
| 4,368,997 | 1/1983 | Shemtov ................................... 600/228 |
| 4,443,128 | 4/1984 | Yamamoto ................................ 403/385 |
| 4,497,092 | 2/1985 | Hoshino ..................................... 24/514 |
| 4,573,452 | 3/1986 | Greenberg . |
| 4,617,916 | 10/1986 | LeVahn et al. . |
| 4,718,151 | 1/1988 | LeVahn et al. ............................ 24/535 |
| 4,786,022 | 11/1988 | Grieshaber ............................... 248/287 |
| 4,796,846 | 1/1989 | Meier et al. ............................. 248/286 |
| 4,930,932 | 6/1990 | LeVahn .................................... 403/325 |
| 4,949,707 | 8/1990 | LeVahn et al. . |
| 4,971,038 | 11/1990 | Farley . |
| 5,020,195 | 6/1991 | LeVahn ...................................... 24/514 |
| 5,080,088 | 1/1992 | LeVahn . |
| 5,242,240 | 9/1993 | Gorham .................................... 403/391 |
| 5,375,481 | 12/1994 | Cabrera et al. ............................ 74/577 |
| 5,380,338 | 1/1995 | Christian ................................. 606/130 |
| 5,400,772 | 3/1995 | LeVahn et al. . |
| 5,415,159 | 5/1995 | Oritz et al. . |
| 5,741,210 | 4/1998 | Dobrovolny ............................. 600/227 |
| 5,792,046 | 8/1998 | Dobrovolny ............................. 600/234 |

Primary Examiner—Paul J. Hirsch
Attorney, Agent, or Firm—Kinney & Lange, P.A.

[57] ABSTRACT

A clamping device for use in a surgical retractor support includes a first clamp member for clamping a first retractor support. The first clamp member has a first opening that is disposed along a longitudinal axis of the first retractor support for receiving the first retractor support. A pin disposed within the clamp member has a cam surface for acting on the first retractor support member. A handle operable with the pin for moving the cam surface between a first nonlocking position and a second locking position for locking the first retractor support member from movement. Preferably a wedge section is positioned between the cam surface and the first retractor support such that the wedge section frictionally engages the first retractor support when the cam surface is in the second locking position. The clamping device also has a second clamp member for clamping a second retractor support.

4 Claims, 5 Drawing Sheets

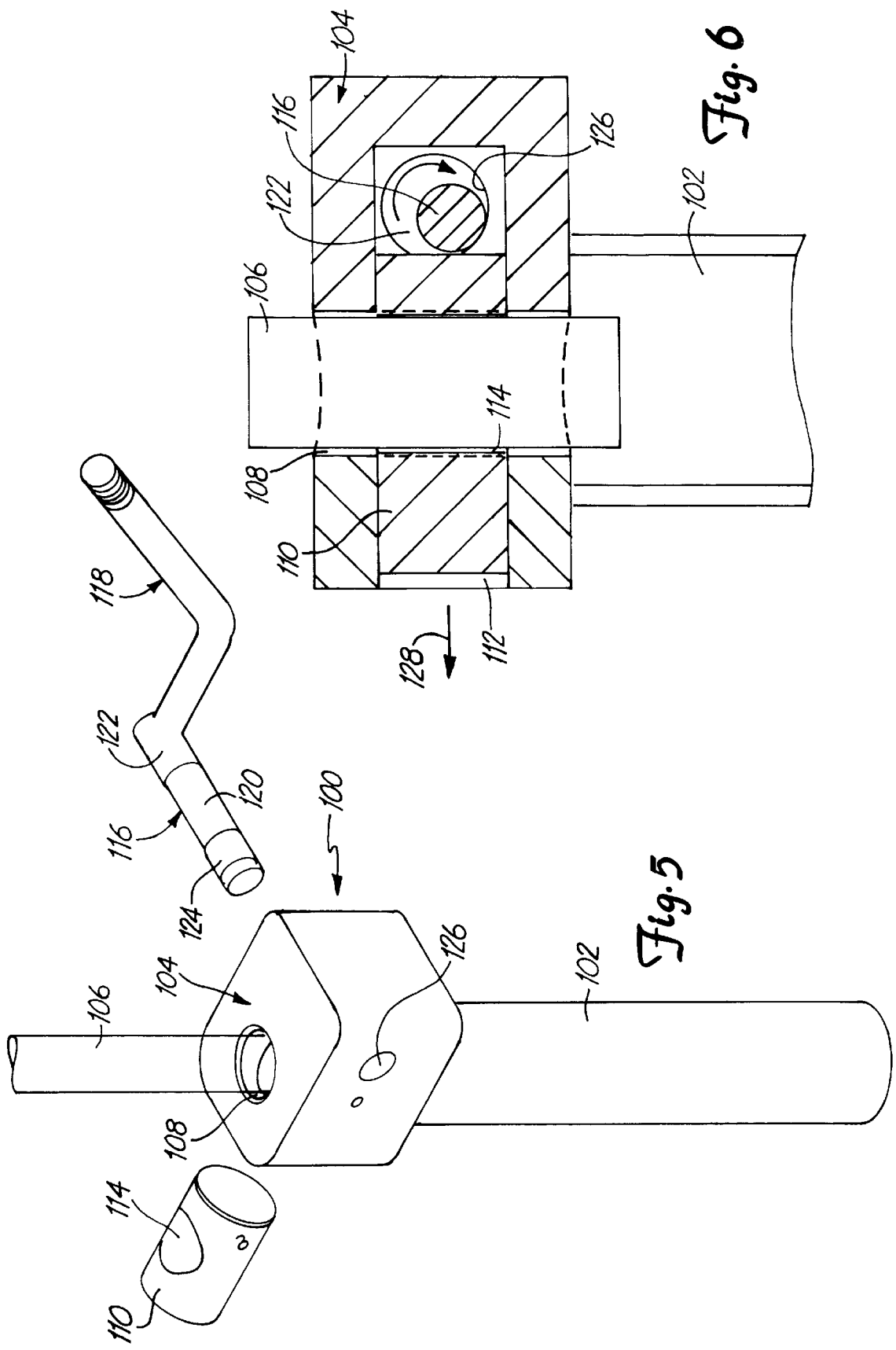

CLAMPING DEVICE FOR A SURGICAL RETRACTOR

CROSS-REFERENCE TO RELATED APPLICATION(S)

This is a continuation-in-part of application Ser. No. 09/048,616 filed Mar. 26, 1998, abandoned which is a divisional of application Ser. No. 08/541,689 filed Oct. 10, 1995, now U.S. Pat. No. 5,741,210.

BACKGROUND OF THE INVENTION

The present invention relates to a surgical retractor apparatus, and more particularly, to a clamping device that supports a retractor apparatus over an operating table.

It is customary during major surgery, particularly on the chest or abdomen, to employ retractors. The retractors are applied to the edges of a surgical incision and pull back the incision thereby exposing an area within the body in which the surgeon must work. The retractor is held in place, typically, by being attached to a retractor support apparatus that is positioned over the operating table. The retractor support apparatus is usually attached to side rails located along the sides of the operating table by some type of clamping device.

In the past, many of the clamping devices on the side rails of the operating table had to be positioned in a precise location. The retractor support apparatus was then secured to the clamping device by various mechanisms to hold the retractor support apparatus in place over the operating table. Since the side rails of the operating table are not sterile, a surgical drape was placed over the side rail by either cutting slits into the surgical drape and extending a support to the retractor apparatus through the slits or simply readjusting the drape around the support and over the clamp and the side rail.

Some of the short comings of the above-mentioned clamping devices are that they do not allow the placement of the retractor apparatus to be varied easily in the horizontal direction along the length of the bed unless slits are made in the surgical drape. However, introducing slits into the surgical drape, to allow the supports of the retractor apparatus to engage the clamping device presents a possible danger of contamination from the unsterile surfaces of the clamping device and the side rail through the slit. In addition, vertical adjustment to the retractor apparatus is difficult since often times the clamping device is beneath the drape.

Simply readjusting the surgical tape around the support member also presents a contamination problem. If the surgical drape is moved or shifts during the operation, the unsterile clamping device and part of the side rail may be exposed.

The following patents assigned to the assignee of the present application illustrate various known clamping devices which are used to support surgical retractors on the side rails of operating tables: LeVahn et al. U.S. Pat. No. 5,400,772; LeVahn U.S. Pat. No. 5,020,195; LeVahn U.S. Pat. No. 4,355,631; LeVahn et al. U.S. Pat. No. 4,949,707; LeVahn et al. U.S. Pat. No. 4,617,916; LeVahn et al. U.S. Pat. No. 4,718,151; LeVahn U.S. Pat. No. 4,930,932; Gorham U.S. Pat. No. 5,242,240, and Christian U.S. Pat. No. 5,380,338.

SUMMARY OF THE INVENTION

The present invention includes a clamping device for use in a surgical retractor support. The clamping device includes a first clamp member for clamping a first retractor support member. The first clamp member has a first opening along the longitudinal axis of the first retractor support member for receiving the first retractor support member. A pin disposed within the clamp member has a cam surface for acting on the first retractor support member. A handle operable with the pin moves the cam surface between a first nonlocking position and a second locking position for locking the first retractor support member from movement in a vertical direction when the first retractor support member is positioned in the first opening.

The clamping device preferably includes a second clamp member for clamping a second retractor support member. The second clamp member includes a first clamping leg extending from the first clamp member and a second clamping leg pivotally mounted to the first clamp member such that the first and second clamping legs are positioned to clamp a second retractor support member therebetween.

BRIEF DESCRIPTION OF THE DRAWINGS

FIG. 5 is a perspective view of an alternative embodiment of the clamping device.

FIG. 6 is a cross sectional view of the clamping device of FIG. 5.

DETAILED DESCRIPTION OF THE PREFERRED EMBODIMENTS

Figure 1:
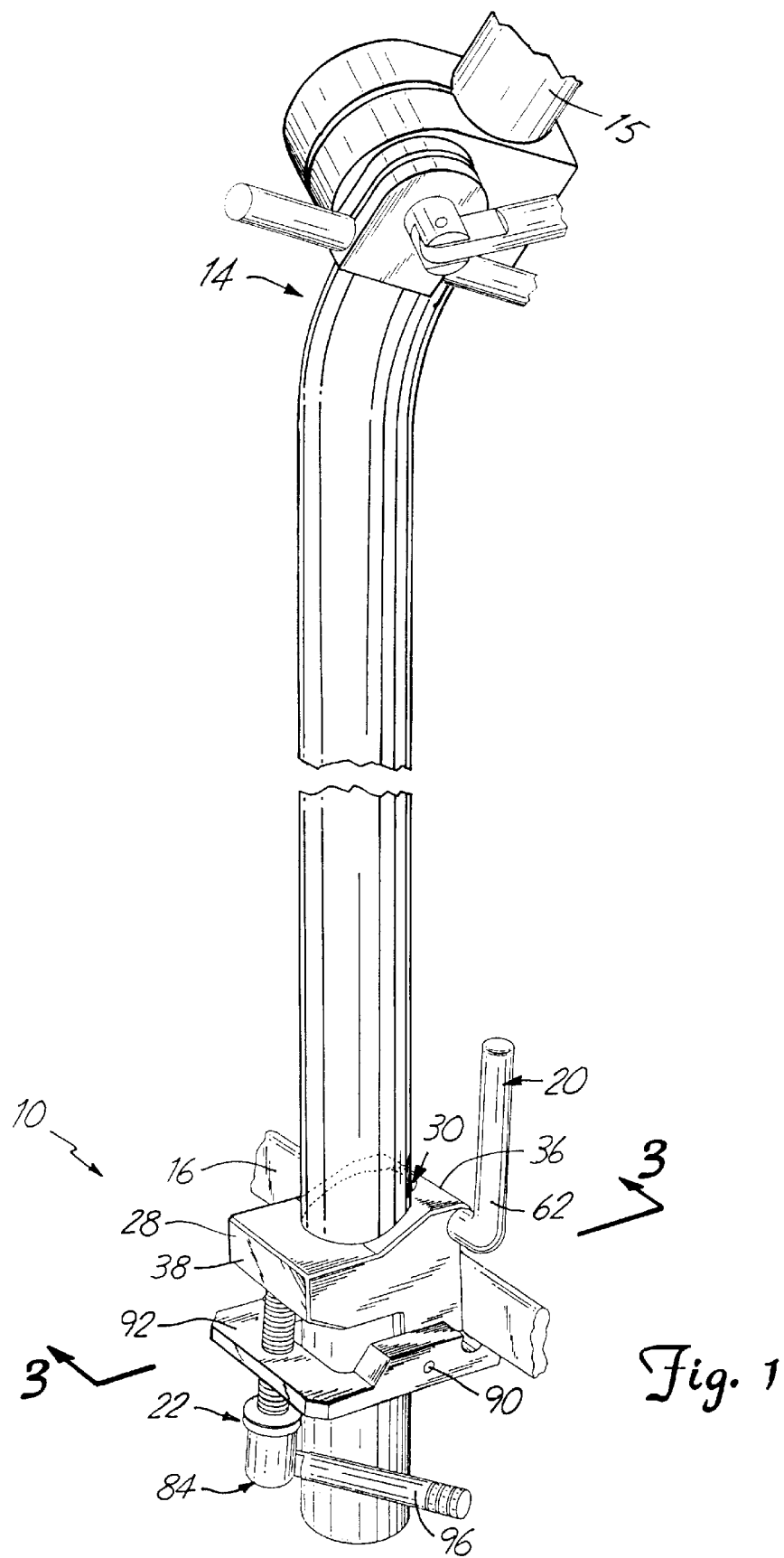
FIG. 1 is an overall perspective view of a retractor apparatus with the clamping device of the present invention.

The clamping device of the present invention is generally indicated at 10 in FIG. 1. The clamping device 10 is used to clamp a retractor (not shown) onto a retractor support 14 that extends over an operating table (not shown). The operating table is a typical operating table onto which the retractor support 14 may be mounted in any desirable or conventional fashion. A typical operating table is illustrated in the LeVahn et al. U.S. Pat. Nos. 4,617,916 and 4,718,151, which are hereby incorporated by reference. It is to be understood that the clamping device 10 of the present invention may be used with most any type of retractor support 14. Preferably, the clamping device 10 is used in combination with a table rail 16 on the operating table and the retractor support 14.

The retractor is employed during major surgery, particularly of the chest or abdomen, and is applied to tissue adjacent a surgical incision to hold back such cut tissue. Holding back the cut tissue exposes an area within the body for the surgeon to work. The clamping device 10 of the present invention permits movement of the retractor along a retractor support tube 15, which is part of the retractor support 14, generally, and the table rail 16, in a quick and efficient manner before or during surgery.

Figure 2:
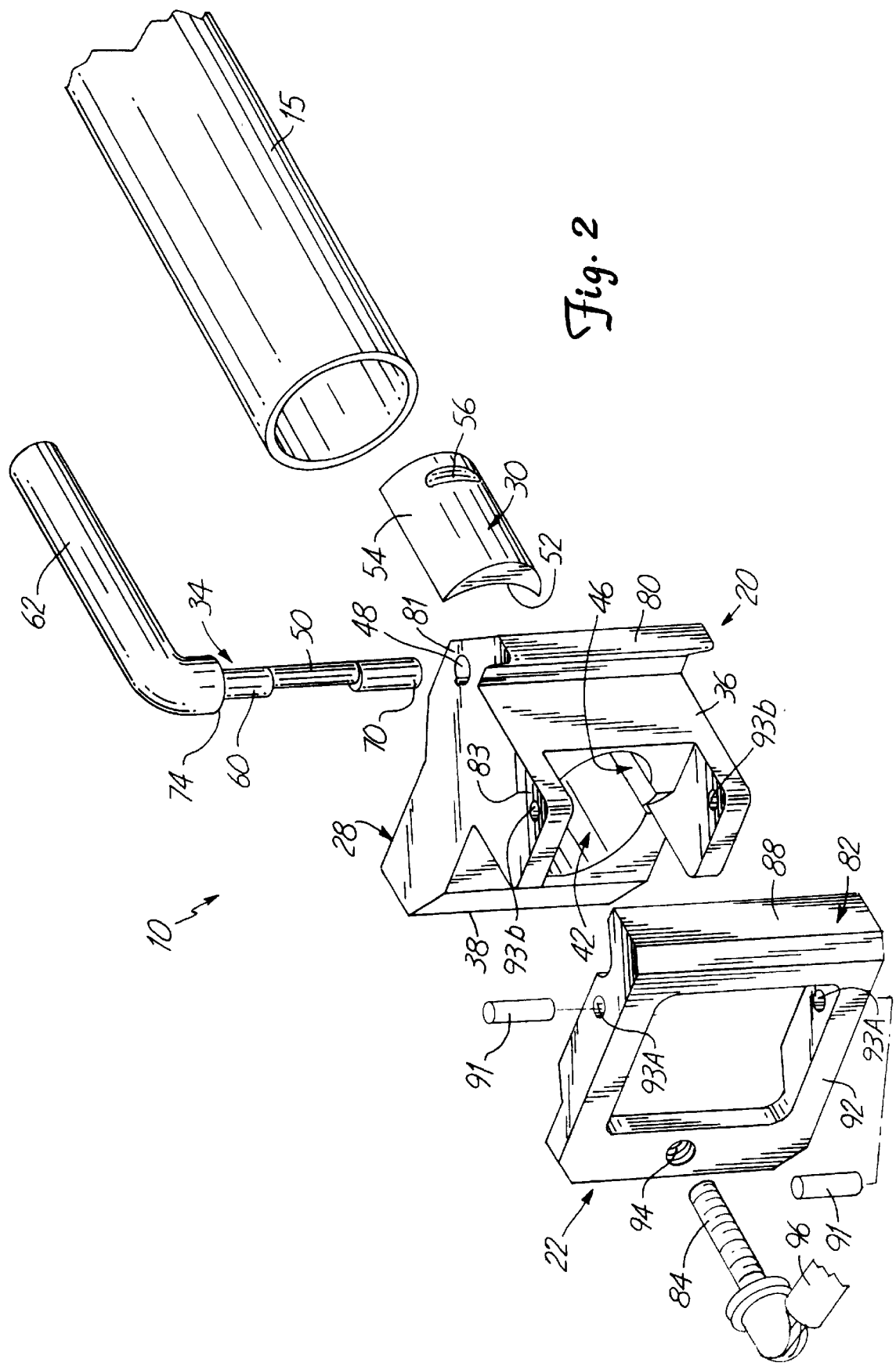
FIG. 2 is an exploded perspective view of the clamping device.

Referring to both FIGS. 1 and 2, the clamping device 10 includes a first clamp member 20 for clamping the retractor support tube 15 and a second clamp member 22 for clamping the table rail 16. The first clamp member 20 includes a unitary main body 28, a wedge section 30 (illustrated in FIG. 2), and a cam operator 34 (illustrated in FIG. 2).

The unitary main body 28 is preferably machined from a single block of stainless steel to include a head end 36, a tail end 38, first opening 42, a recessed area 46 positioned on the outer periphery of the first opening and extending outwardly therefrom, and a second opening 48. The first opening 42 is machined along a longitudinal axis of the unitary main body 28. The first opening 42 is generally cylindrical for receiving the retractor support tube 15 therethrough. However, the size and shape of the first opening 42 may be varied to accept retractor support tubes of other configurations. The recessed area 46 receives or mates with the wedge section 30. The size and shape of the recessed area 46 may be varied to mate with wedge sections of varying shapes. The first opening 42 is sized sufficiently so that cammed movement of the wedge section 30 in the recessed area 46 frictionally clamps the retractor support tube 15 in the first opening 42.

The second opening 48 of the unitary main body 28 is arranged substantially perpendicular to the first opening 42 for receiving the cam operator 34. The second opening 48 intersects a portion of the first opening 42 so that a cam section 50 of the cam operator 34 is free to operate with the wedge section 30. The cam operator 34 acts against the wedge section 30 to provide a frictional force to engage the wedge section 30 with the retractor support tube 15.

Figure 3:
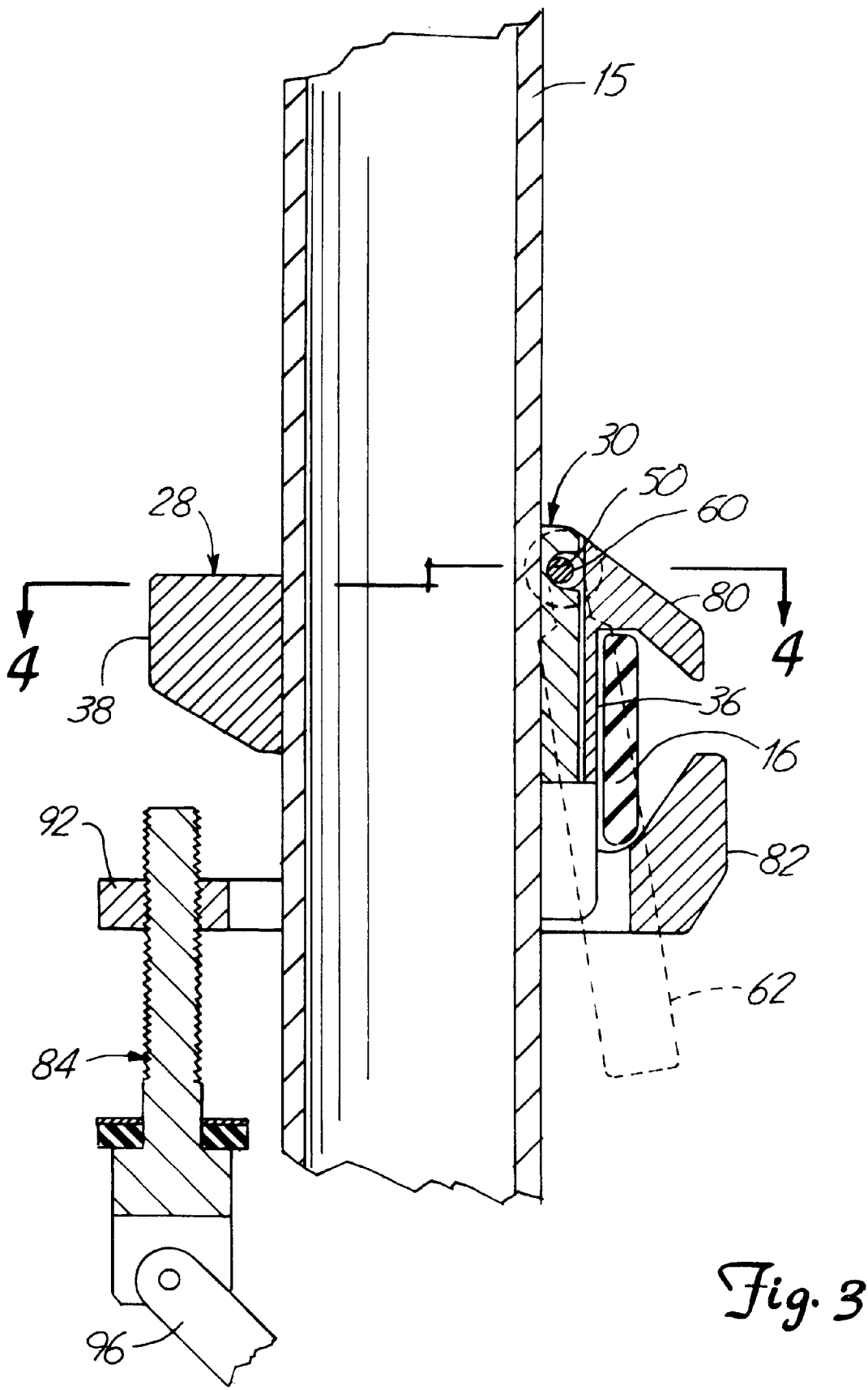
FIG. 3 is a cross-sectional view taken along the line 3—3 in FIG. 1.
Figure 4:
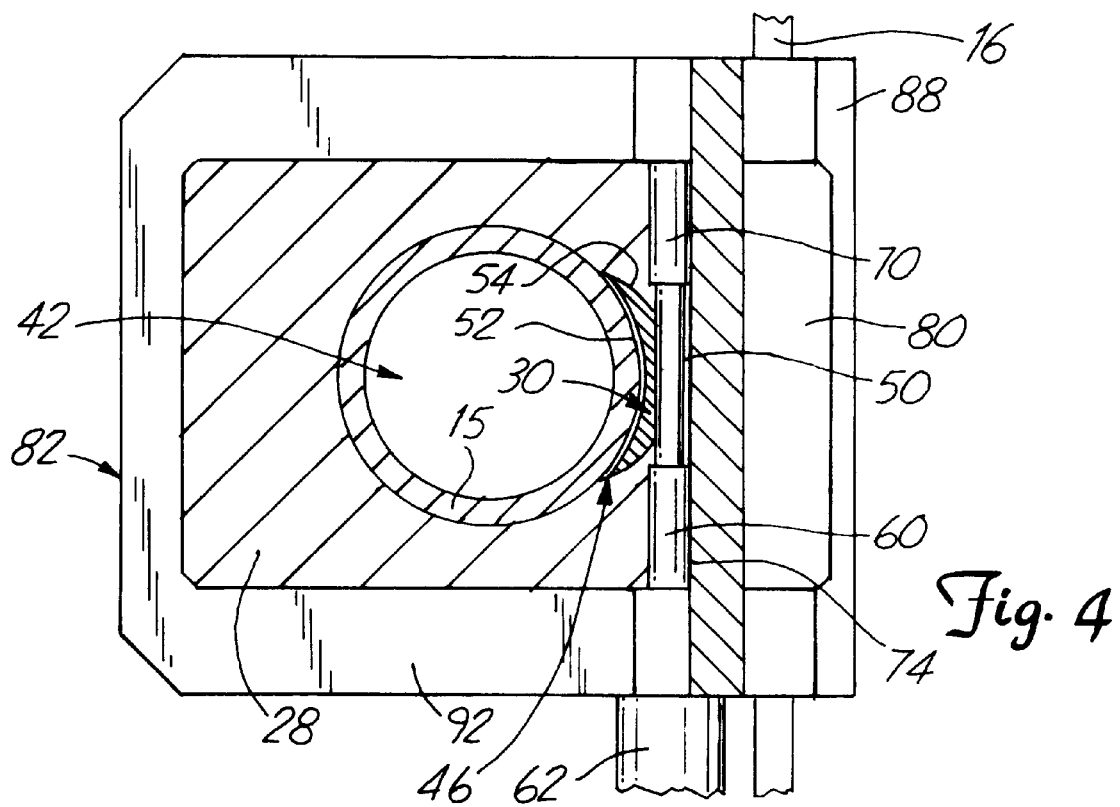
FIG. 4 is a cross sectional view taken along line 4—4 in FIG. 3.

As mentioned above, the wedge section 30 is positioned at the intersection of the first and second openings 42 and 48, in the recessed area 46. The wedge section 30 preferably includes a concave surface 52, convex surface 54, and a recessed channel 56. The concave surface 52 contacts the retractor support tube 15. The convex surface 54 engages the cam operator 34 and is on a side opposite to the concave surface 52 and mates with a surface that defines the recessed area 46. A recessed channel 56 is located on the convex surface 54 and is engaged by the cam section 50 of the cam operator 34. The recessed channel 56 provides an operating area or surface for transferring the frictional force from the cam section 50 to the wedge section 30. FIGS. 3 and 4 illustrate the wedge section 30 in frictional engagement and non-engagement, respectively, with the retractor support tube 16.

Referring back to FIG. 2, the cam operator 34 includes the cam section 50 (previously mentioned), a rod 60, and a lever handle 62. The rod 60 is positioned in the second opening 48 of the unitary main body 28. The cam section 50 is located generally centrally on the rod 60. The cam section 50 has a smaller diameter than the remainder of the rod 60 and an axis that is sufficiently offset from the primary axis of the rod to form a cam. The cam section 50 is positioned at the intersection of the first and second openings 42 and 48 so that the cam section 50 operates with the recessed channel 56 of the wedge section 30. A lock washer or other fastening device (not shown) may be positioned at a distal end 70 of the rod 60 for securing the free end of the rod 60 in the second opening 48. However, the use of such a fastening device is not necessary since engagement of the wedge section 30 with the cam section 50 is sufficient to hold the rod 60 in place.

The lever handle 62 is attached to a proximal end 74 of the rod opposite of the distal end 70 to form, in combination with the rod 60, an "L" shaped arrangement. The lever handle 62 is manually operated to provide a turning force to the rod 60 for engaging the cam surface 50 with the wedge section 30. The cam action forces the wedge section 30 into frictional engagement with the retractor support tube 15 for securing the vertical position of the tube 15 thereof. FIGS. 3 and 4 illustrate the respective engagement and non-engagement positions of the wedge section 30. Since the lever 62 need only be moved a short distance (no more than 90 degrees, and typically only about 30 degrees or less), the present invention provides a quick and easy clamp for securing the retractor support tube 15. The size and position of the cam surface 50 on the rod 60 determines the distance the lever 62 needs to be moved between engagement and non-engagement. The smaller the diameter of the cam section 50 with respect to the diameter of the rod 60, the greater the distance the lever 62 has to be moved and vice versa.

The second clamp member 22 includes an upper clamping leg 80, a lower clamping leg 82, and a locking bolt 84. The upper clamping leg 80 extends outwardly from and is preferably integrally formed with the unitary main body 28 of the first clamp member 20. The upper clamping leg 80 preferably extends across the main body 28 in a continuous length extending from a bottom edge portion 81 of the unitary main body 28. The upper clamping leg 80 extends upwardly and outwardly from the bottom edge 81 of the unitary main body 28 at a angle of approximately 45 degrees.

The lower clamping leg 82 is pivotally mounted to a top edge portion 83 of the unitary main body 28. The upper and lower clamping legs 80 and 82 are arranged in opposing relationship to frictionally clamp the table rail 16 by pivotal movement of the lower clamping leg 82 towards the upper clamping leg 80. The lower clamping leg 82 includes a first portion 88 on a first side of a pivot joint 90 for engaging the table rail 16 and a second portion 92 on an opposite side of the pivot joint 90. The first portion 88 is angled slightly towards the upper clamping leg 80 and is illustrated as having a continuous length along the width of the main body 28. It is understood that while the upper and lower clamping legs 80 and 82 are illustrated as continuous and smooth lengths, other engaging mechanisms such that pinch or have protrusions may be used. The second portion 92 is substantially "U-shaped" wherein the open end of the "U" is closed by the first portion 88. The first and second portions 88 and 92 surround the retractor support tube 15. The pivot joint 90, includes a pin or pair of pins 91 which are operable within openings 93A in the second portion 92 of lower clamping leg 82 and corresponding openings 93b in an upper portion of the unitary main body 28.

The locking bolt 84 is disposed in a threaded opening 94 on the "U-shaped" portion 92 of the upper clamping leg 80 for engaging the tail end 38 of the unitary main body 28 to thereby pivot the lower clamping leg 82 about the pivot joint 90 and clamp the table rail 16 between the upper and lower clamping legs 80 and 82. To facilitate turning the locking bolt 84, a handle 96 is pivotally attached to the locking bolt by a pin 98. The handle 96 is pivotable about the pin 98 from one side of the locking bolt 84 to the other side of the locking bolt 84 or approximately 180 degrees to facilitate turning with the locking bolt 84.

In use, the clamping device 10 of the present invention provides a mechanism for clamping a retractor to a retractor support in a quick and efficient manner. To attach the clamping device 10 to a retractor support 14, a retractor support tube 15 is positioned in the first opening 42 of the unitary main body 28 and the desired height selected as illustrated in FIGS. 1 and 4. In order to position the retractor support tube 15 in the first opening 42, the lever handle 62 is moved so that the cam surface 50 moves the wedge in minimal frictional contact with the tube 15. When the retractor support tube 15 is moved to a selected position, the lever handle 62 is moved in a direction that rotates the cam surface 50 in the recesses channel 52 pushing the wedge section 30 into frictional engagement with the tube 15. As illustrated specifically in FIG. 3, this frictional contact forces the wedge section 30 into frictional engagement with the retractor support tube 15.

The upper and lower clamping legs 80 and 82 are loosely positioned around the table rail 16. The handle 96 is used to turn the locking bolt 84 through the threaded opening 94 of the upper clamping leg 82 until such time as a bottom end of the locking bolt 84 contacts the tail end 95 of the unitary main body 28. At this time, further turning of the handle pivots the first portion 88 of the lower clamping leg 82 around the pivot joint 90 so that the table rail 16 is engaged between the upper clamping leg 80, the lower clamping leg 82, and the head end 36 of the unitary main body 28.

In an alternative embodiment, a clamping device is generally indicated at 100 in FIG. 5. It will be appreciated that the clamping device generally indicated at 100 is an alternative embodiment to the main body 28 illustrated in FIGS. 1 through 4. The clamping device I 00 may be configured so that it is usable with the lower clamping leg 82 as illustrated in FIGS. 1 through 4. The clamping device 100 includes a lower support post 102 and a clamping block 104. An upper post 106 extends through a first clamping bore 108 within the block 104. A dog 110 is disposed within a chamber 112 that is disposed transversely to the bore 108 and communicates with the bore 108 such that the dog 110 moves across the bore 108. The dog 110 includes a second clamping bore 114 through which the upper post 106 also extends.

The clamping device 100 further includes a cam mechanism 116. The cam mechanism 116 includes a handle section 118, a camming element 120 and coaxially disposed cylindrical sections 122 and 124 with the camming element 116 positioned therebetween. The clamping block 104 includes a cam bore 126 that is disposed transversely to the chamber 112 such that when the camming device 116 is inserted into the cam bore 126, the camming element 116 is positioned within the chamber 112.

As best illustrated in FIG. 6, the camming element 120 is positioned to engage the dog 110. When the handle 118 is turned, the camming mechanism 116 is thereby turned. The cylindrical sections 122 and 124 rotate coaxially within the bore 126 and position the camming element 120 to engage the dog 110. When the dog 110 is engaged by the camming element 120, the dog 110 moves in the general direction indicated by arrow 128 thereby moving the post 106 against the surfaces of the first clamping bore 108 frictionally clamping the upper post 106 and locking the post 106 in a selected vertical position.

Although the present invention has been described with reference to preferred embodiments, workers skilled in the art will recognize that changes may be made in form and detail without departing from the spirit and scope of the invention.

We claim:

1. A clamping device for use in a surgical retractor support which includes a retractor support member, the clamping device comprising:

a clamp member for clamping the retractor support member, the clamp member having a first opening therethrough disposed along a longitudinal axis of the retractor support member for receiving the retractor support member;

a pin disposed within the clamp member, the pin having a cam surface for maneuvering the retractor support member; and a handle operable with the pin for moving the cam surface between a first position and a second locking position for locking the retractor support member from movement when the retractor support member is positioned in the first opening.

2. The clamping device of claim 1 and further including a chamber and a dog positioned within the chamber such that the cam surface of the pin acts on the dog moving the dog to lock the retractor support member in a selected position.

3. The clamping device of claim 2 wherein the dog includes a bore through which the retractor support member extends, and wherein when the dog is moved, the retractor support member is frictionally retained from movement.

4. A clamping device for use in a surgical retractor support which includes a retractor support member, the clamping device comprising:

a clamp member for clamping the retractor support member, the clamp member having an opening therethrough disposed along a longitudinal axis of the retractor support member for receiving the retractor support member;

a pin disposed within the clamp member, the pin having a cam surface for providing a force to clamp the retractor support member; and a handle operable with the pin for moving the cam surface between a first position and a second locking position for locking the retractor support member from movement when the retractor support member is positioned in the opening.

\* \* \* \* \*